United States Patent [19]

Nagasaki et al.

[11] Patent Number: 4,602,281
[45] Date of Patent: Jul. 22, 1986

[54] AUTOMATIC MEANS FOR CONTROLLING DOSAGE OF ILLUMINATING LIGHT FOR PICKING-UP IMAGE BY ENDOSCOPE ASSEMBLY

[75] Inventors: Tatsuo Nagasaki, Musashino; Hiroyoshi Fujimori, Hachioji, both of Japan

[73] Assignee: Olympus Optical Co., Ltd., Tokyo, Japan

[21] Appl. No.: 646,332

[22] Filed: Aug. 31, 1984

[30] Foreign Application Priority Data

Sep. 5, 1983 [JP] Japan .................. 58-163597

[51] Int. Cl.$^4$ .............................................. H04N 7/18
[52] U.S. Cl. ......................................... 358/98; 128/6; 358/41; 358/168
[58] Field of Search ................. 358/98, 168, 1, 41; 128/6

[56] References Cited

U.S. PATENT DOCUMENTS 4,074,306  2/1978  Kakinuma ........................ 128/6
4,532,918  8/1985  Wheeler .......................... 358/168
4,535,758  8/1985  Longacre ......................... 358/168

FOREIGN PATENT DOCUMENTS 3118341  2/1982  Fed. Rep. of Germany ......... 128/6

Primary Examiner—Howard W. Britton
Attorney, Agent, or Firm—Armstrong, Nikaido, Marmelstein & Kubovcik

[57] ABSTRACT

The invention relates to means for controlling automatically the intensity of illuminating light for picking up an object to be observed by an endoscope assembly to an level suitable for the observation of object by controlling the output from power source for actuating the light source by the electrical signals issued correspondingly to the dosage on a solid pickup element. The means receive the electrical signals issued from the solid pickup element to form brightness signals, which are applied on the power source for actuating the light source to control the output therefrom depending on the level of brightness signals, thereby controlling automatically the illuminating intensity of light issued from the light source to a level suitable for picking up the image of object.

5 Claims, 4 Drawing Figures

AUTOMATIC MEANS FOR CONTROLLING DOSAGE OF ILLUMINATING LIGHT FOR PICKING-UP IMAGE BY ENDOSCOPE ASSEMBLY

BACKGROUND OF THE INVENTION

The present invention relates to an automatic means for controlling the dosage of illuminating light projected onto an object to be observed. The brightness is controlled to be suitable for the observation of said object and to prevent the blooming phenomenon.

It is well known to employ a solid state image sensing element incorporated in an endoscope assembly to display the image of an object on a display mans such as a cathode ray tube or the like.

An electronic endoscope assembly incorporating such a solid-state image sensing element is advantageous in that the image can be recorded easily and it will be miniaturized more compactly with progress in the integration technique as compared with conventional systems focussing an optical image through an image-guiding fiber bundle.

When such a solid-state image sensing element is employed and if the incident dosage on the receiver element on the receiving surface is excessively high, an electric charge corresponding to said dosage leaks to the periphery and results in spreading or the blooming phenomenon to make the correct reproduction of an image impossible at these spots and also to make the receiving impossible until the restoration to the normal light conditions.

In order to prevent such blooming phenomenon, it has been proposed to adjust the brightness of the illuminating light mechanically at the light source side. However, when an endoscope assembly is employed in a cavity of a living body, the brightness should be adjusted depending on the distance to an object to be observed, or when the tip of insert member is bent, the distance to the wall of cavity in the living body is varied complicatedly so that it is substantially impossible to adjust the illustrating brightness to a proper level in a short interval.

In addition, when the assembly is employed in the cavity of a living body and when the diseased site is moistened by the body fluid, the reflecting brightness is increased and the proper illustrating brightness depends on the condition of diseased site. On the contrary, when the illustrating brightness is excessively small, the diseased site cannot be photographed distinctly to allow a proper diagnosis.

SUMMARY OF THE INVENTION

It is thus a principle object of the present invention to provide means for automatically controlling the dosage of illuminating light received by an endoscope assembly. It is another object of the present invention to provide means for automatically controlling the dosage of illuminating light to the brightness suitable to be received by the solid-state image sensing element. It is a further object of the present invention to provide means for automatically controlling the dosage of illuminating light suitable for providing the observed image with contrast suitable for the diagnosis with an endoscope assembly.

Other advantages and features of the present invention will become clear in view of the following disclosure.

DETAILED DESCRIPTION OF THE PREFERRED EMBODIMENTS

Figure 1:
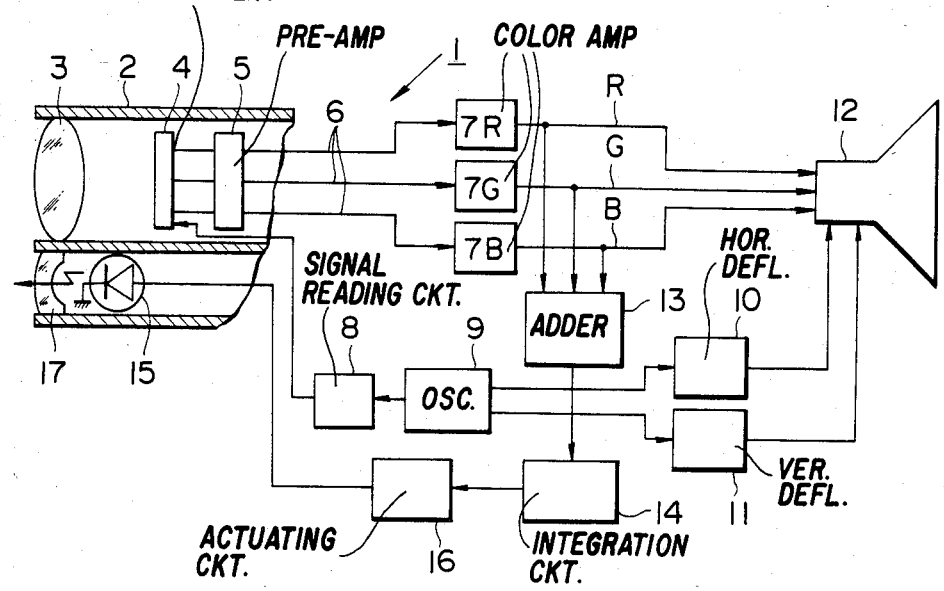
FIG. 1 is a schematic diagram of a first embodiment of the present invention, illustrating the structure of an endoscope assembly provided with means for automatically controlling the illuminating dosage.

An endoscope assembly 1 provided with the first embodiment as a shown in FIG. 1 is incorporated with an objective lens system 3 for focussing the image at the tip side of insert member 2 having a small diameter and a solid-state image sensing element 4 such as charge-coupled device (CCD) or the like so that objective lens system 3 is focussed on the surface of the solid-state image sensing element. A tri-color mosaic filter (not shown) is attached in contact with the focal plane of said solid-state image sensing element 4 for transmitting only light having respective wave length through each mosaic filter portion. There are a large number of receiver elements having photoelectric conversion activity on the focal plane of the solid-state image sensing elements. By applying clock signals to the solid-state image sensing element, signals corresponding to the picture elements passing through red, green or blue transmitting filters are issued successively from the three output terminals thereof, amplified through a preamplifier 5 having a low noise factor, passed through signal cables 6 and amplified further through trailing color amplifier 7R, 7G or 7B.

The clock signals are formed by the reference signal in a reference oscillator 9 and issued from a signal reading circuitry (actuation circuitry) 8 to be applied to said solid-state image sensing element 4 for reading the signal corresponding to each colored picture element.

Said reference signal is supplied respectively to a horizontal deflection circuitry 10 and vertical deflection circuitry 11 for forming horizontally and vertically deflected signals. Each deflected signal is applied to the X- and Y-deflection terminal of color cathode-ray tube 12 and the red, green and blue color signals R, G and B issued from each color amplifier 7R, 7G or 7B are swept horizontally and vertically to be displayed on color cathode-ray tube 12.

On the other hand, said endoscope assembly 1 is incorporated with automatic means for controlling the illuminating dosage. The means are composed of an addition circuit 13 for adding color signals R, G and B issued from said color amplifiers 7R, 7G and 7B to form brightness signals and an integration circuit 14 for integrating signals from said addition circuitry 13 to issue signals for controlling the dosage of illuminating light. The controlling signals issued from said integration circuitry 14 are applied to the control terminal of light source actuating circuit 16 for controlling the luminance intensity (illuminating intensity) of an incandescent lamp or luminous diodes 15 as a light source. The automatic controlling means are composed of said means for controlling the dosage of illuminating light and light source actuating circuit 16.

Luminous diodes 15 as an example of a light source comprise normally multiple sets of three diodes and issue white light including wave lengths of the three primary colors. They are attached at the tip of insert member 2 for illuminating the object through light distributing lens system 17 so that it may be observed over the range capable of being focussed by objective lens system 3.

Figure 2:
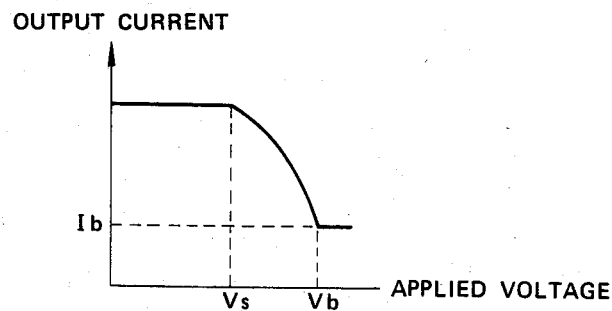
FIG. 2 illustrates a characteristic curve showing the relation between the voltage applied to the controlling terminals of light source actuating circuitry comprising means for automatically controlling the dosage vs. the output current of the first embodiment of FIG. 1.

As shown in FIG. 2, said light source actuating circuit 16 acts, for example, to vary the output current by the voltage applied to the controlling terminal. In other words, when the voltage applied to the controller increases beyond a threshold value $V_s$, the amplification degree of output current is reduced correspondingly to the level of applied voltage to control the current (or voltage) supplied to luminous diodes 15. In addition, when the applied voltage is increased beyond a level $V_b$ ($V_b > V_s$) when the blooming phenomenon may occur, the output current is reduced to a level $I_b$ to reduce the illuminating intensity to maintain the illuminating intensity at a constant level so no blooming will occur. In addition, in said integration circuit 14, the time constant is set to a time limit capable to read the signals of a total receiver element in solid-state image sensing element 4, namely to a duration of approximately one frame. Such a duration is based on the fact that the output signals read by each receiver element correspond to the total dosage received during one frame duration.

The operation of the first embodiment comprising the aforementioned members will now be described. Said endoscope assembly 1 is inserted into a cavity of living body and the tip of insert member 2 is secured so as to easily observe an object such as diseased site on the cavity.

The signals received by each receiver elements in solid-state image sensing element 4 and converted into electrical signals under the illumination from luminous diodes 15 are read successively by the clock signals, amplified through preamplifier 5 and color amplifiers 7R, 7G and 7B and displayed on monitoring color cathode-ray tube 12 by being swept by the horizontally and vertically deflected outputs. Luminous diodes 15 emit illuminating light at the maximum intensity under normal conditions. When the illuminating strength is increased excessively by the tip of endoscope assembly being positioned too near to the diseased site, or by the excessive reflection of light by a portion of the diseased site or by other causes, the output signals from the receiver elements in solid-state image sensing element 4 come to a higher level to increase levels of color signals R, G and B issued from at least one of color amplifiers 7R, 7G and 7B, thereby increasing the level of signals formed by adding the color signals to convert them into brightness signals and by integrating the brightness signals. The output current from light source actuating circuitry 16 is controlled by the level of signal for controlling the illumination so that it is reduced.

Hence, when the added output provided by adding the color signals R, G and B issued from color amplifiers 7R, 7G and 7B through added adder 13 has an excessively large wave form incapable of being observed easily in the absence of automatic control, the signals are added and integrated to provide a higher output level. The output current from light source actuating circuitry 16 is then reduced quickly as shown in the characteristic curve of FIG. 2, thereby controlling the illuminating intensity so that it is reduced automatically to an illuminating level capable of being observed easily.

In other words, the means control the illuminating intensity to a level suitable for observation. Moreover, when the illuminating strength is increased further to a level higher than $V_b$ where the blooming phenomenon tends to occur, the output current from light source actuating circuit 16 is controlled quickly to a constantly low level to maintain the illuminating intensity at a constant value.

Accordingly, when the dosage received by solid-state image sensing element 4 is excessively high such that the possibility of the blooming phenomenon exists, the illuminating intensity is controlled automatically and quickly so as not to cause the blooming phenomenon.

By the provision of such means for automatically controlling the intensity of illuminating light, when the operator changes the position of insert member 2 so that he can observe the object such as diseased site or the like easily, the illuminating intensity is controlled automatically and quickly to be set to a suitable level without causing the blooming phenomenon.

Thus, a physician can be provided with an image having easily observable contrast and which would therefore allow a more correct diagnosis to be made. In addition, he does not need to manually adjust the illuminating intensity, and thus he can devote himself entirely to diagnosis or treatment.

Figure 3:
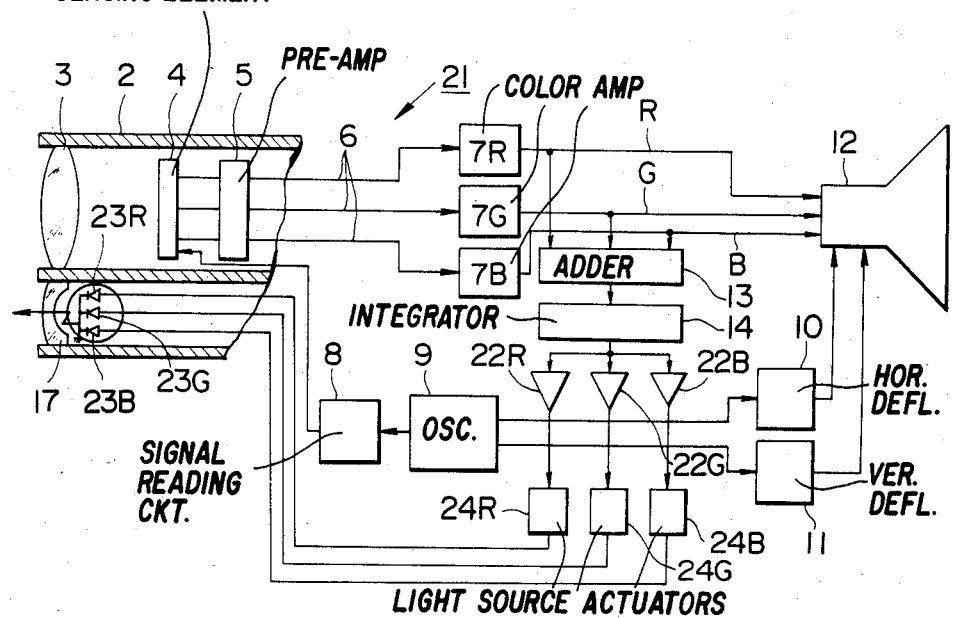
FIG. 3 is a schematic diagram illustrating a second embodiment of the present invention.
Figure 4:
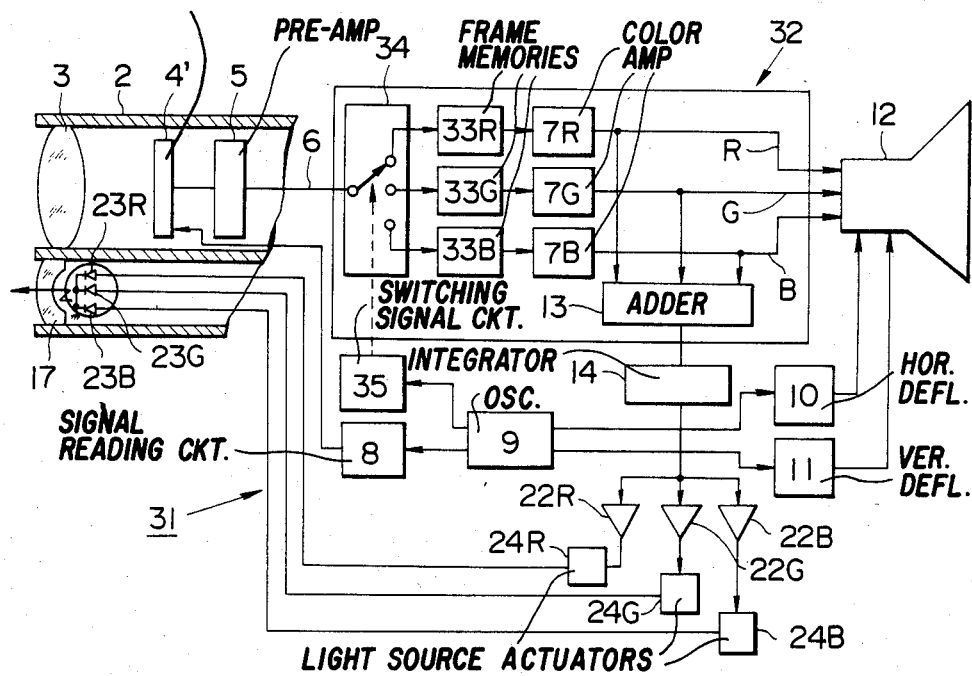
FIG. 4 is a schematic diagram illustrating a third embodiment of the present invention.

The structure of the endoscope assembly in accordance with the second embodiment as shown in FIG. 3 will now be described.

The means for controlling the illuminating intensity in endoscope assembly 21 comprises controlling by calibrating colors of each wave length.

The output terminals of color signals R, G and B from color amplifier 7R, 7G and 7B are connected through adder 13 and integration circuit 14 with each input terminal of amplifier 22R, 22G and 22B for calibrating the colors. The outputs from amplifiers 22R, 22G and 22B comprise signals for controlling the intensity of illuminating light and said signals are applied to the controlling terminals of light source actuating circuits 24R, 24G and 24B for supply actuating powers to luminous diodes 23R, 23G and 23B issuing red, green and blue light having the corresponding wave lengths. Said amplifiers 22R, 22G and 22B function to calibrate the illuminating characteristics of luminous diodes 23R, 23G and 23B employed as the light sources, photosensitive characteristics for the wave length or color of solid-state image sensing element 4 and to fix the amplifications partly at suitable levels. In some case, the color amplifier may be replaced by attenuators.

The other members are constructed similarly to those in the first embodiment and the same members are attached with the same abbreviations as to those in the first embodiment. According to the endoscope assembly incorporated with the second embodiment, the illuminating intensities are automatically controlled by color calibrating each color signal so that the illuminating intensities can be controlled with color tone with higher fidelity as compared with the first embodiment.

The following description illustrates the structure of endoscope assembly in accordance with the third embodiment. Endoscope assembly 31 employs monochrome solid-state image sensing element 4 including three primary color filters. The object is illuminated successively with light having wave lengths corresponding to the three primary colors and the received signals under the illumination of three types of monochromatic light are written on each frame memories 33R, 33G and 33B in video-processor means 32 through multiplexer 34. The written signals are immediately read from each frame memory to be displayed on color cathode-ray tube 12.

Luminous diodes 23R, 23G and 23B are actuated subsequently by the power supplied by each light source actuating circuit 24R, 24G or 24B and the timing is carried out by switching signals from reference signals from reference oscillator 9. Automatic means for controlling the intensity of illuminating light have similar members to those in the second embodiment. The color signals from the output terminals of color amplifiers 7R, 7G and 7B are passed through adder 13 to be converted into brightness signals which are then integrated through integration circuitry 14. The output current from light source actuating circuits 24R, 24G and 24B are controlled by the outputs from calibration amplifiers 22R, 22G and 22B.

Frame memories 33R, 33G and 33B may be capable of retaining in memory the analog amounts. When they are capable of retaining in memory digital amounts such as in a random access memory, dynamic memory, etc., the analog amounts are converted to digital amounts through an A/D converter prior to being retained in memory and the memory output is converted to the analog amounts through a D/A converter to be displayed.

When a digital memory is employed, the address signals for writing and reading are provided, for example, by dividing the clock signals for reading the signals applied to solid-state image sensing element 4. In this embodiment, when the signal levels stored in each frame memories 33R, 33G or 33B are excessively larger, they are automatically controlled to prevent the blooming phenomenon and to a proper illuminating intensity. Hence the displayed image has moderate contrast and each color is calibrated and automatically controlled so that the color tone can be reproduced with high fidelity.

In addition, by said endoscope assembly 31, not only a colored image but also monochromatic images are displayed on monitoring color cathode-ray tube 12.

It should be noticed that the present invention is not limited to the above-mentioned embodiments. A light guide may be used in lieu of luminous diodes 15 in the first embodiment and the power to the light source lamp may be controlled for illuminating the input end of said light guide. Such a light guide may be applied not only for the color photography but also for the black and white or monochromatic image.

Furthermore, means for taking the signals corresponding to each picture element from each receiver elements formed on the focal plane of solid-state image sensing element 4 or 4' to enable the display on color cathode-ray tube 12 or the like are not limited to those disclosed hereinabove. As mentioned hereinabove, according to the present invention, when an object to be observed is illuminated by means of an illuminating light source and the image focussed on the focal plane of a solid-state image sensing element through a focussing optical system, the illuminating intensity from the light source is controlled depending on the output signal from each receiver element attached to said focal plane so that the blooming phenomenon can be prevented by a simple mechanism and the illuminating intensity is controlled automatically to the optium intensity when the distance to the object is changed to facilitate the observation or diagnosis with easily observable contrast.

Accordingly, an operator is free from troublesome operation for controlling the illuminating intensity manually to devote himself to the correct diagnosis or therapeutical treatment.

It is obvious to design various embodiments and modifications of the present invention without departing from the spirit and scope of the present invention so that the present invention should not be constructed to be limited to any particular embodiments except the limitations specified by the attached claims.

What is claimed is:

1. A system for automatically controlling the intensity of illuminating light in an endoscope assembly with an elongated insert member insertable into a cavity, said system comprising:

a variable intensity light source unit disposed at a tip of said insert member to vary the intensity of illuminating light in response to the application of a current or voltage thereto, said light source unit providing a plurality of different light colors;

an objective optical system disposed at the tip of said insert member for focussing the image of an object to be observed onto a focal plane;

a solid-state image sensing element disposed in said insert member, said sensing element having receiver elements disposed in said focal plane to provide a photoelectric conversion of the incident light on said receiver elements;

an actuating circuit means for providing signals corresponding to said receiver elements by the application of clock signals to said sensing element;

display means for displaying output color signals from said sensing element;

controlling means for providing control signals for controlling the intensity of said light source including, (a) adder means for adding said color signals, and (b) integrating means for integrating the output signals from said adder means; and a light source actuating means connected to color outputs of said controlling means and to terminals of said light source for actuating said different colors of said light source individually and automatically in order to control the illumination intensity therefrom.

2. Means according to claim 1 wherein said light source comprises a plurality of incandescent lamps.

3. Means according to claim 1 wherein said controlling means includes color calibrating means for calibrating the illuminating characteristics of said light source, and photosensitive characteristics of said solid pickup element.

4. Means according to claim 1 wherein said light source comprises luminous diodes issuing three primary colors.

5. Means according to claim 4 wherein said light source actuating means includes three light source actuating circuits for actuating the luminous diodes emitting each color of three primary colors.

* * * * *